(12) United States Patent
Hobo (10) Patent No.: US 6,328,563 B1
(45) Date of Patent: Dec. 11, 2001

(54) DENTAL SHADE SYSTEM (75) Inventor: Sumiya Hobo, Tokyo (JP)

(73) Assignees: GC Corporation; Sumiya Hobo Research Associate, both of Tokyo (JP)

( * ) Notice: Subject to any disclaimer, the term of this patent is extended or adjusted under 35 U.S.C. 154(b) by 0 days.

(21) Appl. No.: 09/609,031

(22) Filed: Jun. 30, 2000

(30) Foreign Application Priority Data

Jul. 2, 1999 (JP) .................................... 11-189039

(51) Int. Cl.[7] .................................... A61C 19/10

(52) U.S. Cl. .................................... 433/26

(58) Field of Search .................................... 433/26, 203.1; 434/98, 99, 100, 101; 356/421, 423

(56) References Cited

U.S. PATENT DOCUMENTS

| | | | |
|---|---|---|---|
| 4,657,399 | * | 4/1987 | Hall ...................................... 356/421 |
| 4,802,850 | * | 2/1989 | Boon ...................................... 433/26 |
| 5,149,267 | * | 9/1992 | Longhini et al. ...................... 433/26 |
| 5,261,815 | * | 11/1993 | Pozzi .................................... 433/26 |

* cited by examiner

Primary Examiner—Todd E. Manahan
Assistant Examiner—Melba Bumgarner
(74) Attorney, Agent, or Firm—Oblon, Spivak, McClelland, Maier & Neustadt, P.C.

(57) ABSTRACT

A dental shade system that includes one or more triangular pillars on three faces of which many different color samples are arranged and by which the natural tooth color can be compared with the color samples with one or two actions and decided visually in terms of three coordinates in color space, in order of Value (lightness), Chroma (color saturation), and Hue (color).

11 Claims, 5 Drawing Sheets

DENTAL SHADE SYSTEM

BACKGROUND OF THE INVENTION

1. Field of the Invention

The present invention relates to a dental shade system for measuring natural tooth color, by classifying natural tooth colors in terms of three dimensional coordinates of Value, Chroma, and Hue and by arranging dental color samples (shades) equidistantly in vision.

2. Description of the Conventional Art

Dental shade systems (in other words, dental shade guides) are dental systems composed of color samples necessary to meet a patient's satisfaction by matching the color of dental prostheses including artificial teeth to the patient's natural tooth color, improving prostheses esthetically. In the process of fabricating dental prostheses, information of the patient's tooth color is required to be included in the instructions written in a prescription card sent from the dentist to the laboratory technician. Therefore, in a dental clinic, it is indispensable to be able to select the color which matches the patient's natural tooth color and send corresponding information to the laboratory. As patients' interest in dental esthetics has increased, the importance of precise information has rapidly increased.

As is generally known, the colors that human eyes sense are described by three dimensional coordinates; Value (lightness level), Chroma (color saturation), and Hue (color). These coordinates have been well known as the Munsell system (Munsell, 1905), by reason of its color samples being arranged with perceptually even spacing. However, with the development of color science, the existence of the inherent chromatic distortions in the color space of the Munsell system became clarified. Spacing the color samples requires a non distorting color space such as the more recently developed and internationally accepted colorimetric for reflective materials, CIELAB (CIE 1978).

However, conventional dental shade guides have not been arranged logically or scientifically and do not even correspond to measured tooth color. Shade guides of all dental restorative materials are based on the long established porcelain shade guides which evolved to represent the available shades of porcelain teeth. The shades developed by a process of popular selection by which shades perceived to be nearer tooth color were added and the least popular eliminated. This concept has not changed since the introduction of porcelain over two hundred years ago.

The color of teeth is limited from yellowish to reddish and occupies about a 1% region of a total color space. Moreover, existing dental shade guides have contained only 6~12% of the 1% region of the total color space mentioned above. In addition, since these dental shade guides have been selected by experience, the distribution of their colors in color space has not been uniform. Accordingly, the result of their use has been incorrect and not effective, so it has been difficult to visually match the color of prostheses to a patient's natural tooth color.

To resolve this problem, in recent years, a dental shade system applying color science was developed by Hall, evaluating existing methods and problems and quantifying the difficulties of color matching. A tooth color order system was developed resulting in the construction of a tooth color atlas assembled for easy use offering the accurate measurement of tooth color and the potential of perfect color matching (Hall 1991 and U.S. Pat. No. 5,498,157).

In the dental shade system developed by Hall, the color samples are arranged like a lattice in color space at equal intervals which are near the threshold value of the ability of human sight to distinguish colors. They consist of Values having 5 steps (marked as 1, 2, 3, 4, and 5 in order of lightness), Chromas having 3 steps (marked as 1, 2, and 3, in order of weak, medium, and strong clearness), and Hues having 3 steps (marked as L, M, and R in order of yellowish, medium, and reddish), totaling 5×3×3=45 color samples as the basic composition of the system. By this composition, a first scientifically reasonable dental shade system which covers the total region of the color distribution of human natural tooth in color space has been actualized. In Table 1, the basic composition of the color sample arrangement of the Hall dental shade system 111 is shown. In the basic composition of the color sample arrangement of the Hall dental shade system shown in Table 1, the colors of each color sample are marked according to Hall's notation. For example, 3M/2 means that the Value of the color sample is 3, the Chroma is 2, and the Hue is M.

The occurrence rate of tooth color in color space is not uniform. When we mark Values having 5 steps as V1, V2, V3, V4, and V5 in order of lightness (corresponding to 1, 2, 3, 4, and 5 mentioned above), the occurrence rate of V1 is 2%, V2's is 26%, V3's is 50%, V4's is 20%, and V5's is 2%, differing largely with each other. Since a similar situation exists for the case of combining Chroma and Hue, it can not be said to be best, in view of a cost versus effect ratio, to compose a dental shade system with many color samples paying attention only to the region of color space that tooth color occupies.

Figure 5:
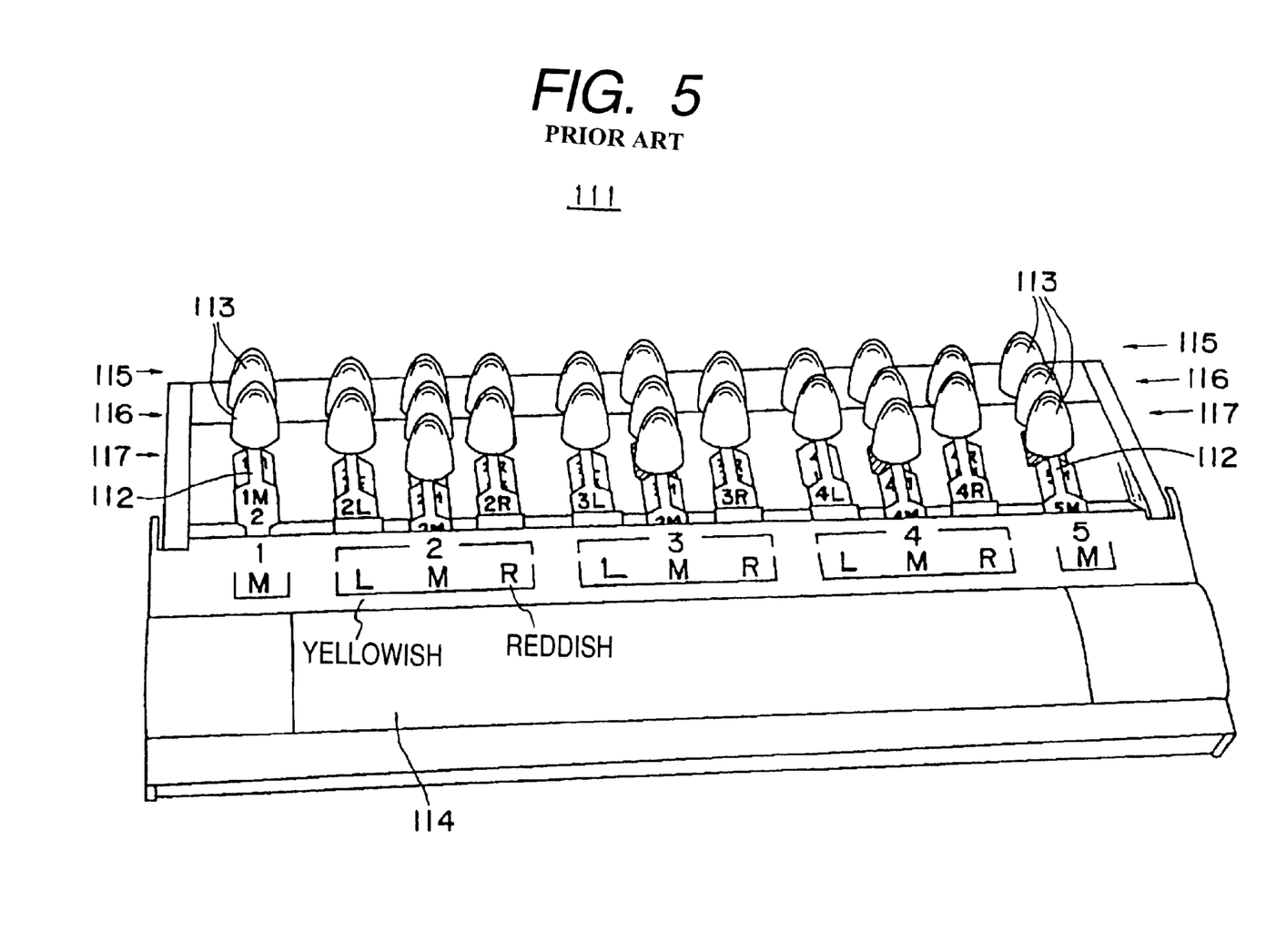
FIG. 5 is a bird's-eye view showing the dental shade system of the conventional art.

For such a practical reason, Hall reduced the number of color samples from the 45 mentioned above to 26, by excluding those color samples the occurrence rates of which are low. As the result, as shown in FIG. 5, the Hall dental shade system 111 is constituted of 11 bundles which are inserted into the color sample rack 114 arranged horizontally and on each bundle two or three color samples 113 are attached in order and a handle 112 is attached at the bottom.

In Table 2, the practical composition of the color sample arrangement of the Hall dental shade system 111 is shown. In Table 2, x marks show 7 among 19 color samples which are excluded due to their low occurrence rates. (The other 12 color samples in rows 1L, 1R, 5L, 5R which are excluded due to their low occurrence rates, are omitted from Table 2).

In relation to the order for visually selecting the color sample the color of which matches the natural tooth color from among the color samples of the dental shade system 111, Hall recommends selecting it in the order of Value, Chroma, and Hue. In the practical composition of Hall dental shade system 111 shown in Table 2, the reason for the color samples 113 having weak Chroma (1 or 1.5) being arranged in the first line 115 (front line 115 in FIG. 5: upper side in the figure) is, that if the color samples had strong Chroma, it would be difficult to decide the Value for the natural tooth by bringing the color sample rack 114 to the patient's natural tooth. In addition, as shown in FIG. 5, the tops of the color samples having medium Hue (M) among the color samples arranged in the first line 115 are projected slightly higher (in FIG. 5) than the tops of the neighboring color samples in the first line 115 so that the visual appearance is not disturbed by the neighboring color samples having yellowish Hue (L) or reddish Hue (R). Moreover, in the practical composition of the Hall dental shade system 111 shown in Table 2, some of Chromas 1 or 3 are replaced by 1.5 or 2.5 where latter marks (1.5 and 2.5) indicate intermediate Chromnas, respectively. The reason for the above replacements is to revise non-uniformity of the distance in color space between residual color samples which has resulted from having color samples with low occurrence rates excluded, as mentioned above.

As described heretofore, the method of deciding the color in terms of Value, Chroma, and Hue by means of comparing the color samples visually with the object, is a classical one known together with the name of the Munsell system. However, the method of this type is, even in the present day, said to be the most superior dental clinical method when compared to modem colorimetrics utilizing electronics, for the reason that the method is extremely low cost, does not need a standard light source or a dark room, and can perform colorimetry visually with high sensitivity.

PROBLEMS TO BE RESOLVED BY THE PRESENT INVENTION

According to recent clinical experiences, it becomes clear that the Hall dental shade system 111 shown in FIG. 5 and described above includes, notwithstanding its highly reasonable composition of color samples applying color science, drawbacks in view of the convenience of its handling as follows.

As described above and shown in FIG. 5 and Table 2, the Hall dental shade system 111 is composed of 26 color samples 113, making 2 or 3 of the color samples which are the same in Value and Hue but different in Chroma each other into a bundle, constituting totally 11 bundles arranged horizontally on a color sample rack 114. At the time of selecting the color sample which matches the natural tooth color, using the dental shade system 111 constituted as described above, the following procedure is recommended. In the first step, select the color sample which matches the natural tooth color in Value, from among the color samples having 5 steps in Value which are arranged on the front line 115 and having weak Chroma (1) and medium Hue (M).

In the second step select the color sample which matches the natural tooth color in Chroma from among the color samples having 2 or 3 steps in Chroma arranged on the same bundle with said color sample selected in the first step.

In the third step, select the color sample which matches the natural tooth color in Hue, from among the three color samples composed of said color sample selected in the second step and the two color samples arranged on both sides of said color sample. While following this procedure, using the color samples of the Hall dental shade system 111 arranged on the color sample rack 114 shown in FIG. 5, there are problems in view of the convenience of handling as follows.

Firstly, for selecting the color sample which matches the natural tooth color in Value, it is necessary to begin by selecting two neighboring color samples having medium Hue (M) from among 11 color samples arranged in order of Value having 5 steps on the front line 115 of the color sample rack 114. Also, in order to decide which color of said neighboring color samples is closer to the natural tooth color in Value, the color sample rack 114 of the dental shade system 111 as shown in FIG. 5 must be brought to the patient's mouth. At that time, since all of the 26 color samples 113 enter into the field of view at one time, it is extremely difficult to decide visually which of said two neighboring color samples matches the natural tooth color in Value. More specifically, the color samples arranged on both sides of each of said two color samples having medium Hue are disturbing because they have different Hues (L or R).

To avoid the difficulty mentioned above, one may choose first to pull out the two bundles on which the two color samples to be compared in Value are arranged and then to compare them by bringing the color sample on the top of each bundle to the patient's mouth, repeatedly. However, that cannot be an efficient method in a clinical situation.

Secondly, for selecting the color sample which matches the natural tooth color in Chroma from among the color samples on the bundle having the Value selected, it is necessary to begin by pulling said bundle out of the color sample rack 114 of the dental shade system 111 shown in FIG. 5, and then bringing it to the patient's mouth, because three color samples having the same Value and different Chroma are arranged in the longitudinal direction of the bundle. However, if the color sample on the top of the bundle is brought to the natural tooth to be compared, the other two color samples are in distant positions from the natural tooth, so it is difficult to compare the three color samples at equal distances from the natural tooth. To avoid this difficulty, the only other choice is to turn the bundle of color samples sideways, and to bring the three color samples to the natural tooth so that they are at the same distance from the natural tooth, resulting in the inconvenience that the color sample resembling the natural tooth in shape is turned sideways. In this connection, although each of the three color samples can be rotated by 90 degrees around the fulcrum of the support plate so that they can be compared with the natural tooth at the same distance and in the same situation with each other, but to handle such manipulations one by one takes time and is not efficient.

Thirdly, for selecting the color sample which matches the natural tooth color in Hue from among the color samples having the Value and Chroma selected, it is necessary to begin by pulling the bundle of color samples (having medium Hue (M)) together with the bundles having yellowish Hue (L) and reddish Hue (R) on both sides of said bundle out of the color sample rack 114 of the dental shade system 111 shown in FIG. 5, and to bring it to the natural tooth to be compared. In this case, to compare color samples with the natural tooth color, holding the three bundles of color samples by hand and keeping each color sample of the three bundles at the same distance and in the same situation with each other is more troublesome than described above, and is entirely inadequate in a clinical situation.

As mentioned above, at the time of comparing the color samples and the natural tooth color, it is necessary to match the longitudinal directions and the situation of the top and the bottom of both. However, in the conventional dental shade system 111, although the shape of the color samples imitates the natural anterior toot the color samples are positioned matching the situation of the top and bottom thereof with the maxillary anterior tooth. Accordingly, the position of the top and the bottom of the color sample rack 114 or the bundle of color sample 112 must be reversed to compare with the mandibular anterior tooth, resulting in extreme inconvenience.

Therefore, although the composition of the color sample arrangement of conventional dental shade system is reasonable in terms of applying color science, the handling method for comparing the color samples with the natural tooth color has not been simple. Moreover, since the color sample arrangement of the dental shade system 111 lacks clearness, user cannot perceive intuitively the three-dimensional character of color which man's eye senses.

SUMMARY OF THE INVENTION

The object of the present invention is to provide a dental shade system, in which the following problems have been solved to overcome the drawbacks of the conventional art described above.

(1) An efficient method, not carried out by inserting many bundles composed of two or three color samples into a color sample rack, but by arranging the color samples separately on one body or plural bodies, so as to enable the user to compare the patient's natural tooth color with the color samples in order of Value, Chroma, and Hue each time by one or two actions, and if necessary, reversing the position of the top and bottom of the color samples by one action.

(2) A simple and clear comparison method, for comparing the patients natural tooth color with a pair of the color samples which differ in Value, Chroma, or Hue each other, in the situation that the other color samples do not enter into the field of vision except said pair of color samples to be compared, and that said pair of color samples and the natural tooth in the field of vision are placed at the same distance from each other, so as to enable the user to compare and decide which of said pair of color samples matches the patient's natural tooth color in Value, Chroma and Hue.

(3) A method, by means of which the user can perceive intuitively that a characteristic of color which mans eye senses is represented by three dimensional coordinates composed of Value (lightness level), Chroma (color saturation), and Hue (color).

In the present invention, there is provided a dental shade system, in which many color samples (shades) are arranged equidistantly (with equal step) visually in color space in terms of three dimensional coordinates of Value, Chroma, and Hue, wherein, many different color samples are placed separately on one or plural narrow triangular pillars, those color samples which are different in plural steps in each of Value or Hue are arranged in order or in combination in the longitudinal direction of said triangular pillar on each of the three faces of said triangular pillar and the color samples having different Chroma in 3 steps are arranged on each of the three faces of said triangular pillars, so that the user can decide the three coordinates of tooth color which match the patient's natural tooth color in Value, Chroma, and Hue.

Therefore, the present invention comprises, instead of adopting the method of the color sample rack in the conventional art, arranging many different color samples separately on one or plural narrow triangular pillars, and arranging the color samples which are different in plural steps in each of Value or Hue in the longitudinal direction on each of the three faces of said triangular pillars in order, and further arranging on each of the three faces of said triangular pillars the color samples each having different Chroma in 3 steps, so that one is enabled to select the color sample which matches the patients natural tooth color, by bringing said triangular pillar to the patient's mouth holding it horizontally with both hands and by moving it to the left and the right (in the longitudinal direction) for selecting the color sample which matches the patients natural tooth color in Value and Hue, and further by rotating said triangular pillar by 120 degrees to the front(clockwise) or back (counterclockwise) for selecting the color sample which matches the patients natural tooth color in Chroma.

As described above, in the conventional art, at the time of comparing the natural tooth color with the bundled color samples 113 arranged on the color sample rack 114, occasionally, the case happens that unnecessary color samples, sometimes all, enter into the field of vision, making it difficult to distinguish visually the two color samples to be compared from among others. Moreover, in the conventional art, there are several ways for comparing the patient's tooth color with color samples and deciding each of the three coordinates of the natural tooth color as follows.

1) To hold and bring all color samples to be compared to the patient's mouth together with the color sample rack on which all color samples are arranged over a broad planar area.

2) To pull out two or three bundles of color samples one by one out of the color sample rack, and hold and bring them to the patient's mouth.

3) To hold sideways one bundle of color samples pulled out of the color sample rack and bring it to the patient's mouth.

4) To rotate the color sample by 90 degrees around the axis of the narrow plate supporting the color sample to the bundle and bring it to the patient's mouth.

Therefore, to select one of the several ways as described above by trial and error in the conventional art, is complicated and troublesome.

On the contrary, as described above in the summary of the present invention, the many different color samples are arranged separately on one or plural narrow triangular pillars, and the way to compare the patient's tooth color with color samples and decide the three coordinates of the natural tooth color, is only composed of picking up, holding, and approaching one of said triangular pillars by both hands to the patient's mouth, and moving it to the left and right (in the longitudinal direction) or rotating it to the front or back by 120 degrees. Therefore, it is a remarkable point of difference between the present invention and the conventional art that the method of comparing tooth color is simple and efficient.

Preferably, in claim 2 of the present invention, all color samples may be arranged on one narrow triangular pillar. On the first face of said triangular pillar, the color samples having weak Chroma and medium Hue are arranged in order of Value, leaving spaces in the longitudinal direction. On both sides of each said color sample, the color samples having the same Value and Chroma as each said color sample and having more yellowish Hue and more reddish Hue than each said color sample (having medium Hue) are arranged, respectively. And further, at the same position as each said color sample in the longitudinal direction, the color samples having the same Value and Hue as each said color sample, are positioned on the second and the third faces of said triangular pillar. And also, in the above, the color samples on the second face have medium Chroma and the ones on the third face have strong Chroma, respectively.

In claim 1 of the present invention described above, there was no regularity in the arrangement of the color samples arranged on said one or plural triangular pillars. However, in the present invention, by arranging the color samples having weak Chroma and medium Hue in order of Value leaving spaces in the longitudinal direction on the first face of said triangular pillar, one is enabled to select the color sample which matches the patient's natural tooth color in Value from among the color samples which are arranged in order of Value on the first face of said triangular pillar, by moving said pillar to the left and right (in the longitudinal direction) in front of the patient's mouth. At that time, since it is difficult to compare Value between the color samples having strong Chroma as mentioned above, in this embodiment, the color samples having weak Chroma are arranged in order of Value on the first face, so that the selection of the color sample by Value become easier. Next, in this first embodiment, the color samples having medium Chroma and strong Chroma are arranged on the second and third faces of said triangular pillar, respectively, so that the color sample which matches the patient's tooth color in Chroma can be selected by rotating said triangular pillar to the front and back by 120 degrees. Further, in this first embodiment, the color samples having yellowish Hue and reddish Hue are arranged on both sides of the color samples having selected Value and Chroma (having medium Hue), so that the color sample which matches the patient's tooth color in Hue can be selected by moving said triangular pillar to the left and right (in the longitudinal direction) easily. As described above, it is a remarkable point of difference between the first embodiment of the present invention in comparison with the summary of the present invention that there is added regularity in the arrangement of the color samples, so that it can be enabled to select the color sample which matches the patient's natural tooth color by deciding three coordinates of the natural tooth color in order of Value, Chroma, and Hue, regularly.

Preferably, in claim 5 of the present invention, as well as in claim 2, all color samples may be arranged on one narrow triangular pillar. On the first face of said triangular pillar, the color samples having weak Chroma and medium Hue are arranged in order of Value leaving spaces in the longitudinal direction. At the same position as each said color sample on the first face in the longitudinal direction, the color samples having the same Value and Hue as each said color sample, are arranged on the second and the third faces of said triangular pillar. Also, in the above arrangement, the color samples on the second face have medium Chroma and the ones on the third face have strong Chroma, respectively. In addition, in claim 5 of the present invention, on both sides of each said color sample, the color samples having more yellowish Hue and more reddish Hue than each said color sample (having medium Hue) are arranged. Together with that, a rotary mechanism by which each position of said color samples having yellowish Hue and reddish Hue can be rotated by hand around the axis of said triangular pillar is added.

In claim 2 of the present invention described above, the color samples having weak Chroma and medium Hue are arranged in order of Value leaving spaces in the longitudinal direction on the first face of said triangular pillar, and the color samples having the same Value and Chroma as each said color sample and more yellowish Hue and more reddish Hue than each said color sample are arranged on both sides of each said color sample, respectively. However, in this arrangement, when the user holds said triangular pillar horizontally and brings its first face to the patient's mouth for selecting the Value of the natural tooth color, the two color samples which have the same Chroma but different Hue lie and enter into the field of vision between the two color samples to be compared in Value, so that simple and clear comparison is disturbed. As described above, it is a remarkable point of difference between the present invention and claim 2 that, on the first face of said triangular pillar, the color samples having different Hue do not lie between the color samples which are arranged in order of Value leaving spaces in the longitudinal direction, so that the visual appearance is not disturbed by the color samples having different Hue, resulting in that simple and clear decision of Value is enabled.

As described above, in the present invention, for making the decision of Value simple and clear, spaces are left on both sides of the color samples having weak Chroma and medium Hue on the first face of said triangular pillar, without positioning any color sample in said spaces left on the first face of said triangular pillar. A rotary mechanism is added to rotate by hand each portion of said spaces left on the first face of said triangular pillar around the axis thereof, for the case that the color sample having weak Chroma arranged on the first face of said triangular pillar is selected, so that one is enabled to compare said color sample having medium Hue with the color samples having yellowish Hue and reddish Hue.

Moreover, on said both sides of the color samples on the second and the third faces of said triangular pillar, the color samples having yellowish Hue and reddish Hue are arranged, with the result that non-uniformity in color space is produced due to the difference of Chroma between the faces. To compensate for that, the medium Chroma (C2) of the color samples on said second face and the strong Chroma (C3) of the color samples on said third face are revised to the intermediate values (C1.5 and C2.5), respectively. Further, in this second embodiment, the addition of the rotary mechanism becomes necessary as described above, resulting in the additive merits that the number of the color samples are enabled to be decreased by excluding the color samples with low occurrence rate and also that the color samples having different Hues from each other are enabled to be compared in the same plane.

In claim 2 the present invention comprises, at the time of selecting Value, Chroma, and Hue in order, first selecting Value by moving said triangular pillar to the left and right (in the longitudinal direction), then after selecting Chroma by rotating said triangular pillar to the front and back by 120 degrees, finally selecting Hue by moving again said triangular pillar to the left and right (in the longitudinal direction) and concluding the selection. During this process, since the actions of selecting Value and Hue are similar, both are likely to be mixed up. Therefore, it is another remarkable point of difference between the second embodiment of the present invention and the first embodiment that the user can perceive intuitively the three-dimensional character of color which man's eye senses through his experience, selecting the Hue by said rotary mechanism the action of which is entirely different from the selecting actions for the Value and Chroma as described above.

Preferably, in claim 8 of the present invention, many different color samples may be arranged separately on four narrow triangular pillars, comprising:

A first triangular pillar, where on the first face among the three faces of said first triangular pillar, the color samples having weak Chroma and medium Hue are arranged in order of Value without spaces in the longitudinal direction, and at the same position as each said color sample in the longitudinal direction, the color samples having the same Value and Hue as each said color sample and also having medium Chroma and strong Chroma, are arranged on the second and the third faces of said first triangular pillar. Also, in the above, the color samples having medium Chroma are arranged on the second face and the ones having strong Chroma are arranged on the third face, respectively.

A second triangular pillar, on the first face among the three faces of said second triangular pillar, the color samples having the lightest Value (V2) among three steps of Value (V2, V3, V4) the occurrence rates of which are high as described above and also having weak Chroma are arranged in order of yellowish Hue, medium Hue, and reddish Hue in the longitudinal direction, and at the same position as each said color sample in the longitudinal direction, the color samples having the same Value and Hue as each said color sample and also having medium Chroma and strong Chroma, are arranged on the second and the third faces of said second triangular pillar. And also, in the above arrangement, the color samples having medium Chroma are stationed on the second face and the ones having strong Chroma are stationed on the third face, respectively.

Third and fourth triangular pillars, the color samples on which are composed of the ones having the Values V3 and V4, respectively, replacing the Value V2 of the color samples arranged on said second triangular pillar, among the Values with high occurrence rate.

Therefore, the present invention comprises, firstly, selecting the first face of said first triangular pillar the color samples on which have weak Chroma and are easily selected in Value, by moving said first triangular pillar to the left and right (in the longitudinal direction), and positioning it so that the natural tooth is located at the intermediate position of two neighboring color samples and in between the Values of which is the Value of the natural tooth color, then deciding which Value of the two color samples is closest to the Value of the natural tooth. Secondly, at the same position as the color sample selected in the longitudinal direction, rotating said first triangular pillar by 120 degrees to the front (clockwise) or back (counterclockwise), then deciding the Chroma which matches the natural tooth color. In this case, it is not possible to compare color samples having different Chromas at the same time in a field of vision, but it is possible to compare them instantly by rotating said triangular pillar by hand as described above.

The present invention comprises, in the case where the Value selected is lower than Values of 3 steps (V2, V3, V4), the occurrence rates of which are low (they are, V1, V5, etc.), finalizing the selection work here, and making the color sample having Value and Chroma selected on said first triangular pillar the color sample of the final selection. In this selection, the Hue of the color sample selected is medium, but since the occurrence rate of the color selected is low, this selection is sufficient in view of color science. On the other hand, in the case where the Value selected is one of V2, V3 or V4, the occurrence rate of which is high, holding said second (V2), third (V3), or fourth (V4) triangular pillar, rotating said (second, third, or fourth) triangular pillar to the front or back by 120 degrees, selecting the face having Chroma selected above on said first triangular pillar, moving said (second, third, or fourth) triangular pillar to the left and right, then selecting the color sample having the Hue which matches with the natural tooth color as a final selection. Thus, the user could finalize the decision of the three coordinates of the patient's natural tooth color in order of Value, Chroma, and Hue, with the result that the decision making for the three coordinates of natural tooth color is simple and clear and does not need any trial and error in each step of the above process in this third embodiment in the present invention.

In another embodiment, in claim 5 of the present invention, selection work is finalized by first taking up said triangular pillar composed of one body and next moving it to the left and right in the longitudinal direction and lastly rotating said triangular pillar (or said rotary portion thereof) to the front and back by 120 degrees. Against the above, in the present invention, since selection work is finalized by first taking up said first triangular pillar and selecting Value and Chroma, next taking up one of said second, third, or fourth triangular pillars depending on the Value selected, and then selecting Hue, so that it seems to be composed of two taking up actions and more complicated than in the first (or second) embodiment. However, in claim 3 of the present invention, in place of one body composition, the number of the color samples to be arranged in the longitudinal direction of said one body (triangular pillar) long. On the contrary, in this third embodiment, since the number of color examples is few, the total lengths of said first to fourth triangular pillars becomes ½–¼ of the former. Therefore, in contrast with the fact that holding said triangular pillar with both hands is necessary in the former case, holding it with one hand is sufficient in the latter case, so that for taking up said triangular pillar each, twice as many actions are necessary for the former case (the first (or second) embodiment) than the latter case (the third embodiment), resulting in compensation of the difference between the two cases in the number of actions described above. It is needless to say that, in comparison between the conventional art or claim 2 and the present invention, the difference between them becomes more remarkable.

In addition to the above, in Claim 5 of the present invention, since trial and error is necessary in every decision stage of Value, Chroma, and Hue, specifically in the stage of comparing Hue, practically speaking, the number of action often exceeds two. However, in the present invention, since trial and error is hardly needed as described above, in almost every decision stage of Value, Chroma, and Hue, the number of actions is sufficient at one or two, including the actions which are to take up one of said first-fourth triangular pillars to bring it to the patient's mouth and to move said triangular pillar to the left and right or to rotate it (or said rotary portion thereof) to the front and back by 120 degrees. This is the first remarkable point of difference in the present invention in comparison with the conventional art or claim 5.

Further, although the shape of the color samples of the dental shade system in the prior art imitates the shape of the natural anterior tooth, the color samples are arranged matching the position of the top and the bottom with the maxillary anterior tooth as described above, so that the position of the top and the bottom of the color samples must be reversed to compare the color samples with the mandibular anterior tooth. In this case, in the prior art, the actions to pass the color sample or the plural bundles of color samples held by both hands conversely are needed. The actions are not only complicated, but even if passing them conversely, the rack of the color sample rack or the handle of the bundle is in the way, causing comparing the natural tooth color with the color samples to be extremely difficult. However, in the present invention, not only all the color samples are arranged on said four triangular pillars each as one body, but each of said four triangular pillars is short, narrow, and light, so that said triangular pillar on which the color samples are arranged can be held by one hand easily and it is enough only to pass the handle of said triangular pillar from one hand to the other (one action) for reversing the position of the top and the bottom of the color As described above, claim 8 of the present invention comprises, instead of inserting many bundles composed of two or three color samples into said color sample rack, arranging them separately on said four triangular pillars, so that one is enabled to compare the natural tooth color with the color samples in Value, Chroma, and Hue in turn by one or two actions, and if necessary, by reversing the position of the top and the bottom of the color samples by one action, providing an efficient method for a dental shade system. Therefore, it could be said that the third embodiment in the present invention fully satisfies the requirements described in the item (1) at the top of this chapter [SUMMARY OF THE INVENTION] as one of three objects of the present invention to overcome the drawbacks in the prior art.

Moreover, in claim 5 of the present invention, since the color samples having weak Chroma and medium Hue are arranged in line in order of Value leaving spaces between them on the first face of said triangular pillar in the longitudinal direction, it is difficult to bring two color samples having different Values and arranged apart to the patients natural tooth close enough to compare them with the natural tooth color for deciding which Value of the two color samples matches the natural tooth color. However, in the present invention, since the color samples having weak Chroma and medium Hue are arranged in order of Value without spaces on the first face of said first triangular pillar, it is easy to bring the two color samples to be compared close enough to the patient's natural tooth, so as to be able to decide precisely which color sample matches the natural tooth color. This is the second remarkable point of difference in claim 8 of the present invention in comparison with claim 3 of the present invention.

Further, in the present invention as described above, since the color samples having medium Hue but not those having yellowish Hue and reddish Hue are arranged on each face of said first triangular pillar, it is needless to say that the color sample which matches with the natural tooth color in Value and Chroma is easily selected unless the visual appearance is disturbed by color samples having different Hue.

As described above, in claim 8 of the present invention, in the process of selecting the color sample which matches the patient's natural tooth color, it is possible to compare simply and clearly a pair of color samples having different Value, Chroma, or Hue as each other with the natural tooth color in Value, Chroma, or Hue, respectively, under the condition that the color samples other than hose to be compared do not enter into the field of vision and said pair of color samples and the natural color are held close together and at an equal distance. Therefore, it could be said that claim 8 of the present invention fully satisfies the requirements described in item (2) at the head of this chapter [SUMMARY OF THE INVENTION] as one of three objects of the present invention to overcome the drawbacks of the prior art.

Further, claim 8 of the present invention as described above comprises, to begin with the first step, selecting the first face of said first triangular pillar on which the color samples have weak Chroma and it is easy to decide color in Value, and moving said triangular pillar to the left and right (in the longitudinal direction) in front of the patient's mouth, then selecting the color sample which matches the natural tooth color in Value. Next, in the second step, rotating said first triangular pillar to the front and back by 120 degrees at the same position (in the longitudinal direction) as the color sample selected in Value in the first step, selecting the color sample which matches the natural tooth color in Chroma. Lastly, in the third step, taking up one of said second, third, and fourth triangular pillars the color samples on which have the same Value as the Value selected in the first step, then starting at the color sample which is on the face having the same Chroma as the Chroma selected in the second step from among three faces of said triangular pillar taken up in the above step, either moving said triangular pillar to the left and right (in the longitudinal direction) by the width of a color sample or doing the same after rotating said triangular pillar to the front and back by 120 degrees, deciding the color sample which matches the patient's natural tooth color in Hue as the final selection.

As described above, in claim 8 of the present invention, one is enabled to decide three coordinates (Value, Chroma, and Hue) of the patient's natural tooth color, in three steps divided clearly, and since deciding the three coordinates is simple and clear and never needs trial and error in every step described above, the user can perceive intuitively the three-dimensional characteristic of color which man's eye senses, represented by three dimensional coordinates composed of Value (lightness level), Chroma (color saturation), and Hue (color). Therefore, it could be said that this fourth alternative as described above fully satisfies the requirements described in item (3) at the bead of this chapter [SUMMARY OF THE INVENTION] as one of three objects of the present invention to overcome the drawbacks of the prior art.

Preferably, in claim 3 of the present invention of the present invention, the numbers of steps of three coordinates of the color samples arranged on said one triangular pillar in claim 2 of the present invention described above may be set at 5 steps for Value, 3 steps for Chroma, 3 steps for Hue, including the whole region of color distribution of the natural tooth. Combining them, the dental shade system in claim 3 of the present invention is composed of 5×3×3=45 color samples at maximum. This composition aims to cover the whole region of color distribution of the natural tooth and also to make uniform the distance in color space between the color samples in vision.

Preferably, in claim 4 of the present invention, by excluding the color samples with low occurrence rates from the color samples arranged on said one triangular pillar in claim 3, the number of color samples may be decreased from 45 at maximum to 26, and the Chromas of a portion of the color samples are revised to intermediate values. This revision is aimed at reducing the cost versus effect ratio by excluding those color samples with low occurrence rates and at revising non-uniformity of distance in vision in color space between the color samples.

Preferably, in claim 6 of the present invention, the number of steps of the color samples arranged on said one triangular pillar in claim 5 of the present invention may be set at 6 steps for Value (adding 1 step whiter than existing tooth color), 3 steps for Chroma, and 3 steps for Hue. Combining them, the dental shade system in claim 6 is composed of 6×3×3=54 color samples at maximum. This composition aims to cover the whole region of color distribution of the natural tooth and also to include 1 step whiter than existing tooth color but the lightest (whitish) color needed in esthetic dentistry.

Preferably, in claim 7 of the present invention, by excluding those color samples with low occurrence rates from the color samples arranged on said one triangular pillar in claim 6 of the present invention, the number of color samples may be decreased from 54 at maximum to 29, and the Chromas of a portion of the color samples are revised to intermediate values. This revision is aimed at reducing the cost versus effect ratio by excluding those color samples with low occurrence rates and at revising non-uniformity of distance in vision in color space between the color samples.

Preferably, in claim 9 of the present invention, the number of steps of color samples arranged on said four triangular pillars in claim 4, may be set 6 steps for Value (adding 1 step whiter than existing tooth color), 3 steps for Chroma, 3 steps for Hue. Combining them, the dental shade system in claim 9 is composed of 18 color samples on said first triangular pillar and 9 color samples on said second, third and fourth triangular pillars each, totaling 18+9+9+9=45 color samples at maximum (including 9 repetitions). This composition is constituted, starting from the arrangement composed of 54 color samples at maximum in the sixth embodiment, in which the whole region of color distribution of the natural tooth is covered and 1 step whiter than existing tooth color is added to Value, decreasing 3(Value)×3(Chroma)×2(Hue)= 18 color samples by reducing the number of steps of Hue from 3 to 1 among the color samples having Value of 3 steps with low occurrence rates, and adding 9 color samples which are in repetition by the reason of arrangement.

Preferably, in claim 10 in the present invention, a further 7 color samples with low occurrence rates may be excluded from 45 color samples (including 9 repetitions) arranged on said four triangular pillars in claim 9 to 38 (including 9 repetitions) color samples, and the Chroma of a portion of the color samples is revised to intermediate amounts. This composition is aimed at reducing the cost versus effect ratio by excluding those color samples with low occurrence rates and at revising non-uniformity of distance in vision in color space between the color samples.

Preferably, in claim 11 in the present invention, the shape and/or material composition of the color samples in the present invention may be made to resemble the natural tooth. This is used in the conventional art also, and is aimed at making it easy to compare the natural tooth color with the color samples and to decrease the influence of a light source, by making the shape and/or material composition of the color samples resemble the shape of the natural tooth (for example: anterior tooth) and/or material composition (for example: dentin and enamel of the natural tooth).

ILLUSTRATION OF NOTATION OF COLOR SAMPLES

V0, V1, V2, V3, V4, V5: steps in Value of color sample
C1, C1.5, C2, C2.5, C3: steps in Chroma of color sample
Y, M, R: steps in Hue of color sample The unit of numerals shows the unit in visual appearance based on the CIEIAB color coordinate system.

DESCRIPTION OF THE PREFERRED EMBODIMENT

The preferred embodiments of the present invention are described according to the attached drawings in the following. In the following description, steps of Value, Chroma, and Hue are set so that the color samples are arranged equidistantly visually. In FIGS. 1–5, the same parts in view of function are designated by the same numerals to omit description thereof.

(The First Preferred Embodiment)

Figure 1:
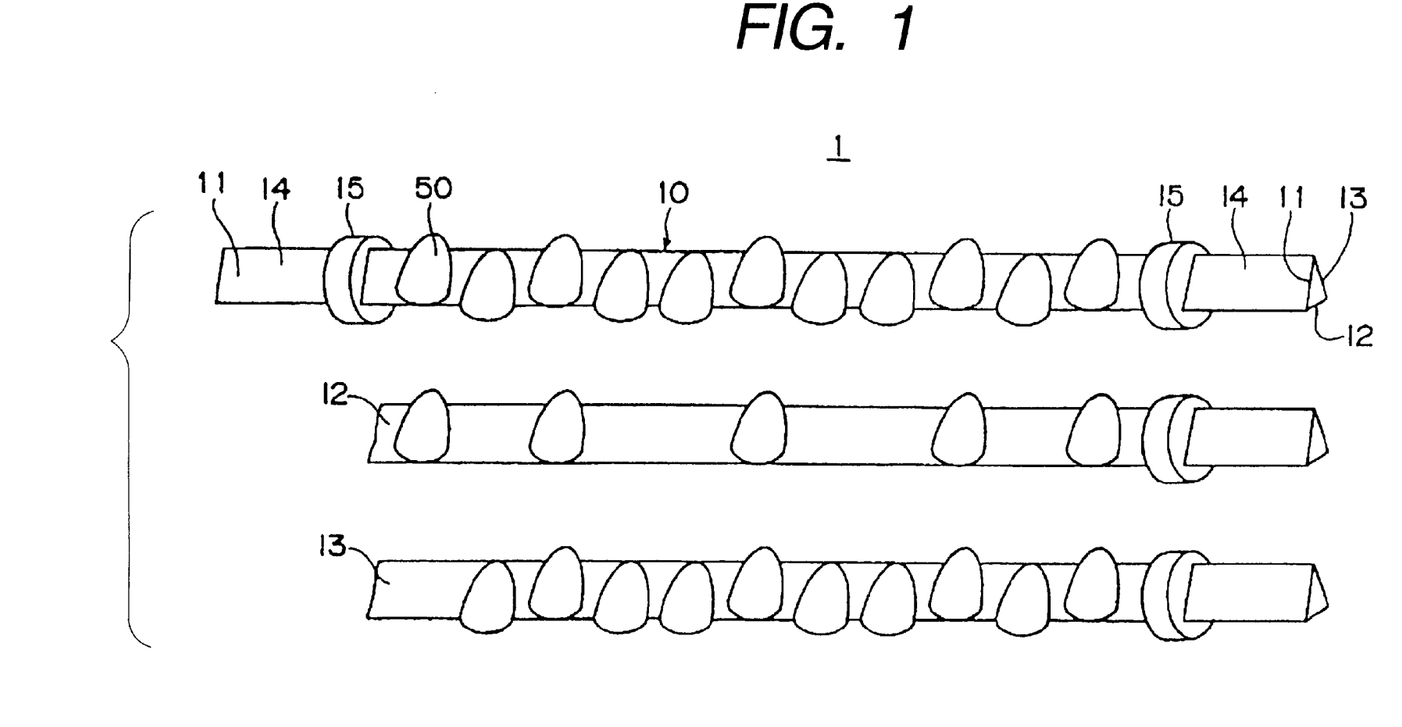
FIG. 1 is a bird's-eye view showing the first preferred embodiment of the dental shade system of the present invention.

FIG. 1 shows the dental shade system 1 of the first preferred embodiment of the present invention. This dental shade system comprises a narrow triangular pillar 10 having handles 14 at both ends, and where on each of three faces 11, 12, and 13 of the triangular pillar 10, eleven positions are set in the longitudinal direction for arranging color samples 50, totaling 11×3=33. In the vicinity of said handles 14, guards 15 are prepared to avoid the finger holding said handle 14 making contact with the color sample 50. These guards 15 are not necessarily prepared.

In the basic composition of the color sample arrangement of the dental shade system 1, as well as the basic composition of the dental shade system 111 in the conventional art shown in Table 1, color samples are put in order combining Value composed of 5 steps (V1, V2, V3, V4, V5, corresponding to the steps of Value 1,2,3,4,5 in the conventional art), Chroma composed of 3 steps (C1, C2, C3, corresponding to the steps of Chroma 1, 2, 3 in the conventional art), and Hue composed of 3 steps of yellowish, medium, reddish (Y, M, R, corresponding to the steps L, M, R in the conventional art), so that totally 5×3×3=45 color samples are arranged. Further, in the practical composition of the color sample arrangement of the dental shade system 1, as well as the practical composition of the dental shade system 111 in the conventional art shown in Table 2, the number of the color samples 50 are reduced from 45 of the basic composition to 26 in the practical composition, by excluding 19 color samples with low occurrence rate.

In Table 3, the color sample arrangement on the first face 11 of the triangular pillar 10 of the dental shade system 1 is shown. On the first face 11 of the triangular pillar 10,' color samples 50 having weak Chroma (C1 or C1.5) are arranged, combining Value of 5 steps and Hue of 3 steps, totally 5×3=15 at maximum, are arranged, reduced finally from 15 to 11 by excluding 4 color samples with low occurrence rates, as shown in Table 3.

In Table 4, the color sample arrangement on the second face 12 of the triangular pillar 10 of the dental shade system 1 is shown. On the second face 12 on the triangular pillar 10, the color samples 50 having medium Chroma (C2) are arranged, combining Values of 5 steps and Hues of 3 steps, totally 5×3=15 at maximum, and finally reduced from 15 to 5 by excluding 10 color samples (including the color samples marked with x) with low occurrence rate leaving spaces as shown by x marks in Table 4.

In Table 5, the color sample arrangement on the third face 13 of the triangular pillar 10 of the dental shade system 1 is shown. On the third face 13 on the triangular pillar 10, the color samples 50 having strong Chroma (C3 or C2.5) are arranged, combining Values of 5 steps and Hues of 3 steps, totally 5×3=15 at maximum, and finally reduced from 15 to 10 color samples by excluding 5 color samples (including the color sample marked with x) with low occurrence rate as shown in Table 5.

As described above, the number of color samples arranged on the three faces 11, 12, and 13 of the triangular pillar 10 of the dental shade system 1 is totally 11+5+10=26, so that the color samples arranged on the first line 115 on the color sample rack 114 of the dental shade system 111 in the conventional art shown in Table 2 are transferred to the first face 11 of the first triangular pillar 10 in the present invention, and also the color samples arranged on the second line 116 are transferred to the second face 12, further the color samples arranged on the third line 117 are transferred to the third face 13.

In the dental shade system 1 constituted as described above, the color sample which matches the natural tooth color is selected by doing as follows.

First, holding the left and right handles 14 of the triangular pillar 10 with both hands, and bringing the first face 11 having weak Chroma (C1) to the patient's natural teeth (maxillary anterior teeth) to be compared, moving to the left and right the triangular pillar 10, then selecting the color sample which matches the natural tooth color in Value among Values of 5 steps (V1, V2, V3, V4, V5) arranged in order of Value. At that time, the user must pay attention only to the color sample 50 having medium Hue (M) among Hues of 3 steps (Y, M, R), and not be disturbed by the color sample having the other Hues. As shown in FIG. 1, among the color samples 50 arranged on the first face 11, the top of the color sample having medium Hue (M) projects a little more than the other color sample on the same line. The reason is that, at the time of selecting Value, the vision is not to be disturbed by the color samples having yellowish Hue (Y) and reddish Hue (R) which are arranged on both sides of the color sample having medium Hue (M).

Secondly, keeping the position of the color sample selected in Value in the longitudinal direction, and rotating the triangular pillar 10 to the front and back by 120 degrees, then selecting the color sample which matches the natural tooth color in Chroma from among the color samples having Chromas of 3 steps (C1, C2, C3).

Thirdly, keeping the position of the triangular pillar 10, and moving it to the left and right, then selecting the color sample which matches the natural tooth color in Hue, from among the color samples having Hues of 3 steps (Y, M, R), and finalizing the selection of the color sample 50 which matches the patient's natural tooth color to be compared.

In some of the color samples 50 in Table 3 and Table 5, weak Chroma (C1) is replaced by an intermediate Chroma (C1.5) which is a little weaker than medium Chroma (C2) and strong Chroma (C3) is replaced by another intermediate Chroma (C2.5) which is a little stronger than medium Chroma (C2). The reason for the replacements is, as described above on the dental shade system in the conventional art, to revise the non-uniformity of distance in vision in color space caused by excluding those color samples having low occurrence rates.

In addition, at the time of selecting the color sample 50, in the case where the patient's natural tooth to be compared is a mandibular tooth, passing the handle 14 of the triangular pillar 10 from one hand to the other, and revising the difference in shape of the top and the bottom between the natural tooth and the color sample.

(The Second Preferred Embodiment)

Figure 2:
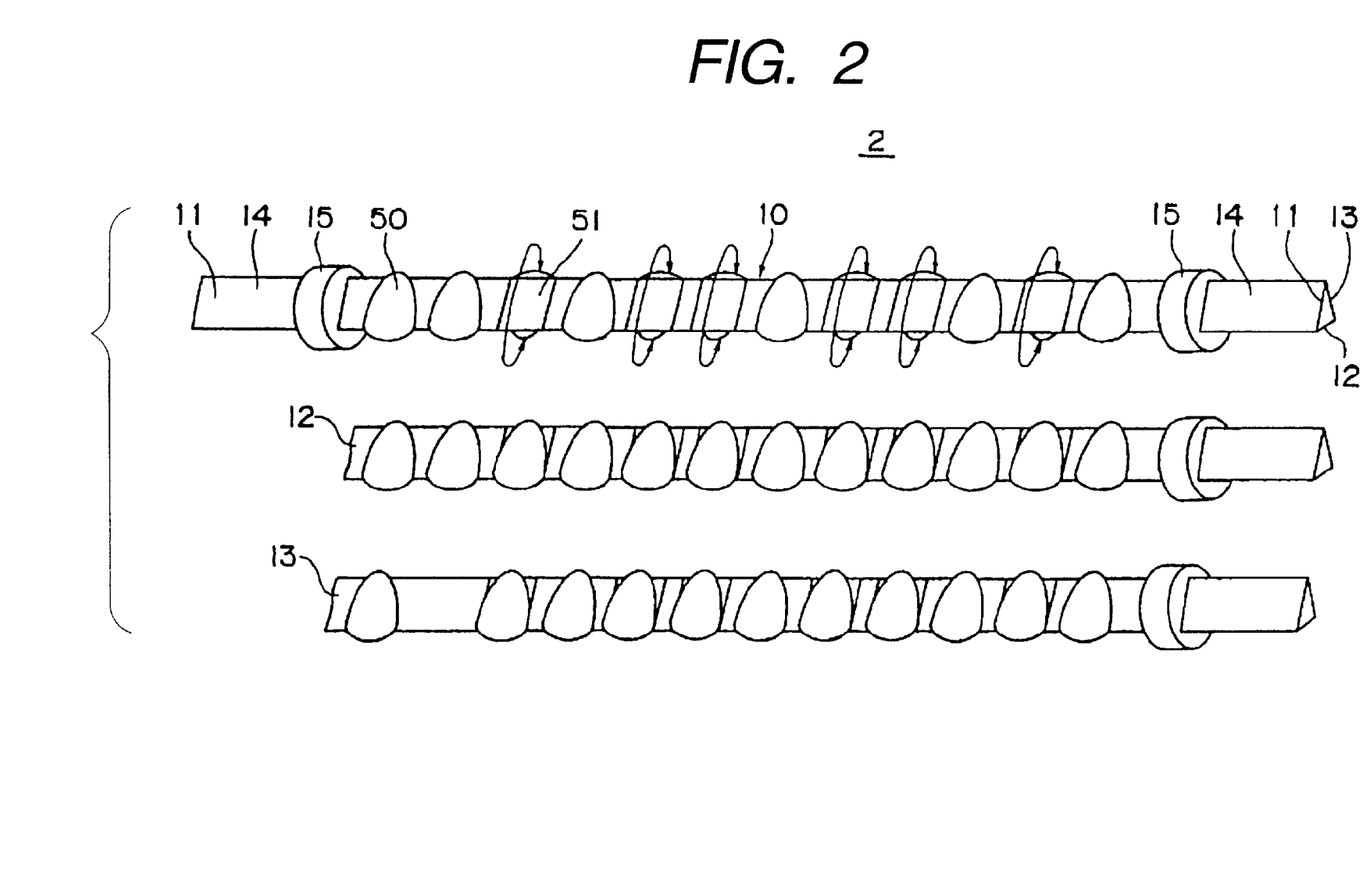
FIG. 2 is a bird's-eye view showing the second preferred embodiment of the dental shade system of the present invention.
Figure 3:
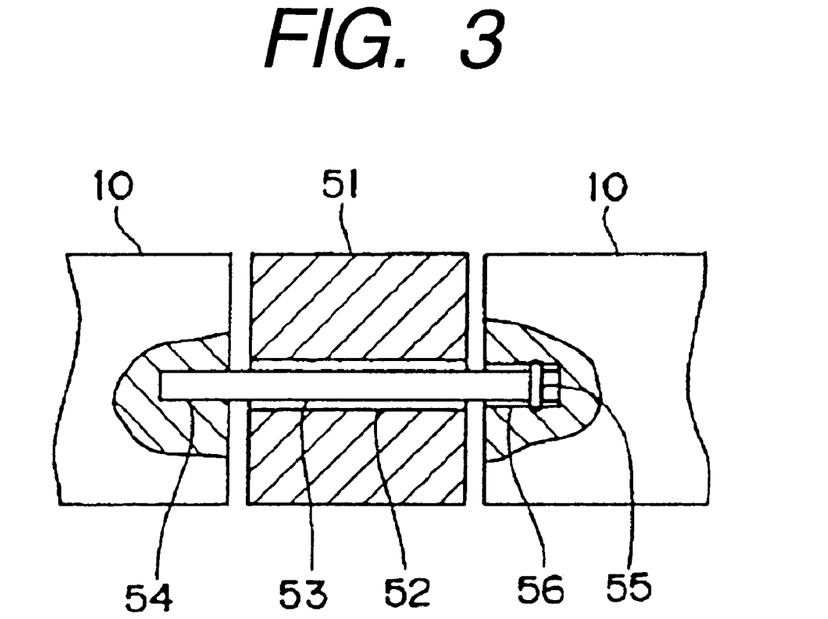
FIG. 3 is a sectional view of the rotating portion in FIG. 2.

FIG. 2 shows the dental shade system 2 of the second preferred embodiment of the present invention. This dental shade system 2 comprises an narrow triangular pillar 10 having handles 14 at both ends, and where, on each of 3 faces (11, 12, 13) of the triangular pillar 10, 12 positions are set in the longitudinal direction for arranging color samples 50, totaling 12×3=36. At each of six positions from among said 12 positions set in the longitudinal direction, a rotary portion 51 is provided as shown in FIG. 3, by forming an axial hole 52 in the center thereof and piercing a pivot 53 through said axial hole 52, and by fixing one end of said pivot 53 piercing into a hole 54 formed on one side of the portion 10, and further by inserting the other end of said pivot 53 having a peripheral projection 55 into a hole 56 formed on the other side of the portion 10, so as to be put on and taken off, or to be fixed. In the resulting arrangement, the rotary portion 51 can be rotated by hand around said pivot 53 independent on both sides of the portions 10.

In the basic composition of the color sample arrangement of the dental shade system 2, color samples are put in order combining Values in 6 steps arranged in order of Values (V0, V1, V2, V3, V4, V5), Chromas in 3 steps of weak, medium, and strong (C1, C2, C3), and Hues in 3 steps of yellowish, medium, and reddish (Y, M, R), so that totally 6×3×3=54 color samples at maximum are arranged. Further, in the practical composition of the dental shade system 2, the number of color samples 50 is reduced from 54 in the basic composition to 29 in the practical composition, by excluding those color samples having low occurrence rates. In addition, as described above, from among said six steps of Value, V2, V3, and V4 are the Values with high occurrence rates. Also, V0 is whiter (lighter) than existing tooth colors, but added in the second preferred embodiment due to the necessity of esthetic dentistry.

In Table 6, the color sample arrangement on the first face 11 of the triangular pillar 10 of the dental shade system 2 is shown. On the first face 11 of the triangular pillar 10 of the dental shade system 2, the color samples 50 having weak Chroma (C1) and medium Hue (M) are arranged in order of Value, combining Values in 6 steps and Hues in 3 steps, totally 6×3=18 color samples at maximum, and finally reduced from 18 to 6 color samples by excluding 12 color samples (including the color samples marked with x) with low occurrence rates, leaving spaces as shown in Table 6 by x marks. In addition, in Table 6, the color sample positions the row numbers of which are circled are said rotary positions 51.

In Table 7, the color sample arrangement on the second face 12 of the triangular pillar 10 of the dental shade system 2 is shown. On the second face 12 of the triangular pillar 10 of the dental shade system 2, the color samples 50 having medium Chroma (C2) or slightly weak Chroma (C1.5) are arranged in order of Value, combining Values in 6 steps and Hues in 3 steps, totally 6×3=18 color samples at maximum, and finally reduced from 18 to 12 color samples by excluding 6 color samples with low occurrence rates as shown in Table 7. In Table 7, the color sample positions the row numbers of which are circled are said rotary In Table 8, the color sample arrangement on the third face 13 of the triangular pillar 10 of the dental shade system 2 is shown. On the third face 13 of the triangular pillar 10 of the dental shade system 2, the color samples 50 having strong Chroma (C3) or a somewhat strong Chroma (C2.5) are arranged in order of Value, combining Values in 6 steps and Hues in 3 steps, totally 6×3=18 color samples at maximum, and finally reduced from 18 to 11 color samples by excluding 7 color samples (including the color samples marked with x) with low occurrence rates as shown in Table 7. In Table 8 the color sample position the row numbers of which is circled is said rotary position 51.

As the result of excluding the color samples with low occurrence rates (including the color samples marked with x) in Table 6, non-uniformity of the distance in visual color space is caused between the remaining color samples. To revise it, in Table 7, in the combination of medium Chroma (C2) with yellowish Hue (Y) or reddish Hue (R), medium Chroma (C2) is replaced by slightly weak Chroma (C1.5). Similarly, in Table 8, in the combination of strong Chroma (C3) with yellowish Hue (Y) or reddish Hue (R), strong Chroma (C3) is replaced by a slightly less strong Chroma (C2.5).

As the final result, the number of color samples 50 arranged on the three faces 11, 12, 13 of the triangular pillar 10 of the dental shade system 2 totals 6+12+11=29.

In the dental shade system 2 constituted as described above, the color sample which matches the natural tooth color is selected by doing as follows.

First of all, holding left and right handles 14 of the triangular pillar 10 with both hands, then adjusting the rotary portions 51 on the triangular pillar 10 by hand so as to match the positions with the arrangement of the color samples shown in Tables 6–8.

For selecting the color sample, first, bringing the face 11 of the triangular pillar 10 on which the color samples having weak Chroma (C1) and medium Hue are arranged in order of Value to the patient's natural tooth to be compared, and moving the triangular pillar 10 to the left and right, then selecting the color sample 50 which matches the natural tooth color in Value, from among Values of 6 steps (V0, V1, V2, V3, V4, V5).

Secondly, keeping the position of the color sample selected in the longitudinal direction, and rotating the triangular pillar 10 to the front and back by 120 degrees, then selecting the color sample 50 which matches the natural tooth color in Chroma among Chromas of 3 steps (C1, C2, C3) arranged on the faces 11, 12, 13 of the triangular pillar 10, respectively.

After that, according to the Value and the Chroma selected, final selection by means of the dental shade system 2 is performed as follows.

(1) In the case where the Value selected is the one of V0, V1, or V5, the occurrence rate of which is low, selecting the color sample 50 having the Value and the Chroma (C1, C2, or C3) selected and medium Hue as the final selection.

(2) In the case where the Value selected is the one of V2, V3, or V4, the occurrence rate of which is high, (a) In the case where the Chroma selected is weak Chroma (C1), rotating each of the rotary positions 51 arranged on both sides of the color sample selected by 120 degrees so that the color sample is arranged side by side with two color samples having a slightly weak Chroma (C1.5) and yellowish Hue (Y) or reddish Hue (R), then deciding which of the three color samples 50 matches the natural tooth color as the final selection.

(b) In the case where the Chroma selected is medium Chroma (C2), deciding which of the three color samples 50 matches the natural tooth color, from among the color sample selected and the two color samples arranged on both sides of it, the latter two of which have a slightly weak Chroma (C1.5) and yellowish Hue (Y) or reddish Hue (R) (on the face 12), as shown in Table 7. When sufficient color matching is not obtained by the above decision work, then rotating each of the two color samples (rotary positions 51) arranged on both sides of the color sample selected by 120 degrees, respectively, and deciding which of the two color samples 50 having a partially strong Chroma (C2.5) and yellowish Hue (Y) or reddish Hue (R) (on the face 13) matches the natural tooth color as the final selection.

(c) In the case where the Chroma selected is strong Chroma (C3), deciding which of the three color samples 50 matches the natural tooth color, from among the color sample selected and the two color samples arranged on both sides of it, the latter two of which have a partially strong Chroma (C2.5) and yellowish Hue (Y) or reddish Hue (R) (on the face 13), as shown in Table 8, as the final selection.

At the time of color selection, in the case where the patient's natural tooth to be compared is a mandibular anterior tooth, revising the difference of the shape between the natural tooth and the color sample by passing the handles 14 of the triangular pillar 10 from one hand to the other.

(The Third Preferred Embodiment)

Figure 4:
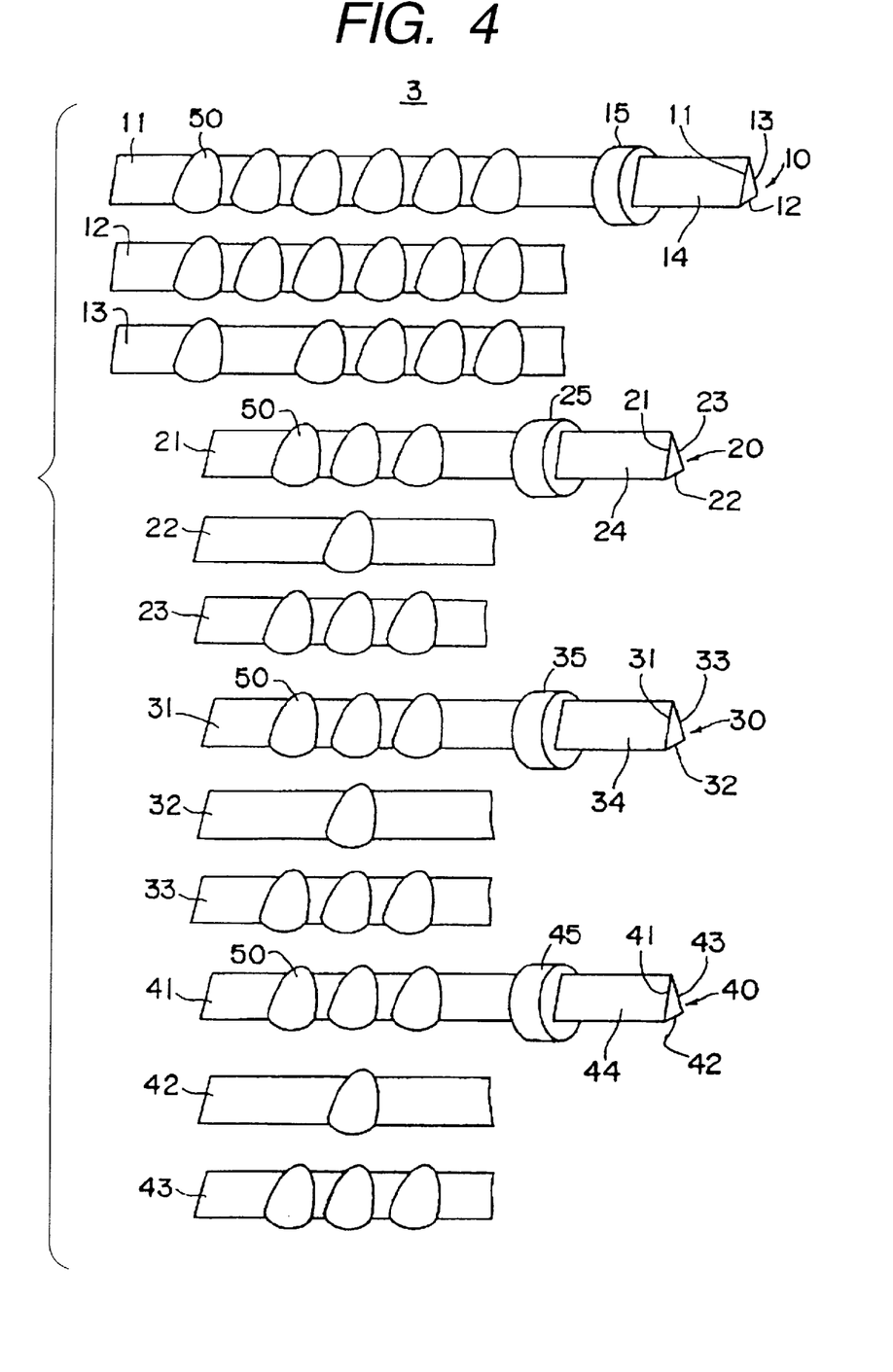
FIG. 4 is a bird's-eye view showing the third preferred embodiment of the dental shade system of the present invention.

FIG. 4 shows the dental shade system 3 of the third preferred embodiment in the present invention. The dental shade system 3 comprises four narrow triangular pillars, comprising, first triangular pillar 10, second triangular pillar 20, third triangular pillar 30, and fourth triangular pillar 40, having handles 14, 24, 34, 44 each on one end and guards 15, 25, 35, 45 each, the arranging positions of the color samples 50 being 6 positions each on three faces 11, 12, 13 of triangular pillar 10, 3 positions each on three faces 21, 22, 23 of triangular pillar 20, 3 positions each on three faces 31, 32, 33 of triangular pillar 30, and 3 positions each on three faces 41, 42, 43 of triangular pillar 40.

The basic composition of the color sample arrangement of the dental shade system 3 is constituted by Values of 6 steps (V0, V1, V2, V3, V4, V5) arranged in order of Value, Chromas of 3 steps (C1, C2, C3) composed of weak Chroma, medium Chroma, strong Chroma, and Hues of 3 steps (Y, M, R) composed of yellowish Hue, medium Hue, reddish Hue, totally 6×3×3=54 color samples at maximum. In the practical composition of the color sample arrangement of the dental system 3, the number of color samples 50 are reduced from 54 in the basic composition to 29 in the practical composition, by excluding 25 color samples with low occurrence rates.

In Table 9, the color sample arrangement on the first triangular pillar 10 of the dental shade system 3 is shown. On the three faces 11, 12, 13 of the first triangular pillar 10 of the dental shade system 3, the color samples 50 having medium Hue (M) and composed in combination of Values of 6 steps (V0, V1, V2, V3, V4, V5) and Chromas of 3 steps (C1, C2, C3), totally 6×3=18 color samples at maximum are arranged, reduced from 18 to 17 by excluding 1 with low occurrence rate shown by an x mark in the Table.

In Table 10, the color sample arrangement on the second triangular pillar 20 of the dental shade system 3 is shown. On the three faces 21, 22, 23 of the second triangular pillar 20 of the dental shade system 3, the color samples having Value V2 which is the first among Values of 3 steps (V2, V3, V4) with high occurrence rates described above and composed in combination of Hues of 3 steps (Y, M, R) and Chromas of 3 steps (C1, C2, C3), totally 3×3=9 color samples at maximum are arranged, reduced from 9 to 7 color samples 50 by excluding 2 with low occurrence rates as shown by x marks in the Table.

As shown by x marks on face 22 in Table 10, the color samples combining medium Chroma (C2) with Hue Y or R are excluded. To revise a non-uniformity of visual color distance caused between the remaining color samples, weak Chroma (C1) combined with Hue Y or R is replaced by slightly weak Chroma (C1.5) on the face 21, and strong Chroma (C3) combined with Hue Y or R is replaced by a partially strong Chroma (C2.5). The same is applied to the triangular pillars 30 and 40 in the following.

In Table 11, the color sample arrangement on the third triangular pillar 30 of the dental shade system 3 is shown. On the three faces 31, 32, 33 of the third triangular pillar 30 of the dental shade system 3, the color samples having Value V3 which is the second among Values of 3 steps (V2, V3, V4) with high occurrence rates described above and composed in combination of Hues of 3 steps (Y, M, R) and Chromas of 3 steps (C1, C2, C3), totally 3×3=9 color samples at maximum are arranged, reduced from 9 to 7 color samples 50 by excluding 2 with low occurrence rates as shown by x marks in the Table.

In Table 12, the color sample arrangement on the fourth triangular pillar 40 of the dental shade system 3 is shown. On the three faces 41, 42, 43 of the fourth triangular pillar 40 of the dental shade system 3, the color samples having Value V4 which is the third among Values of 3 steps (V2, V3, V4) with high occurrence rates described above and composed in combination of Hues of 3 steps (Y, M, R) and Chromas of 3 steps (C1, C2, C3), totally 3×3=9 color samples at maximum are arranged, reduced from 9 to 7 color samples 50 by excluding 2 with low occurrence rates as shown by x marks in the Table.

In the dental shade system 3 constituted as described above, the color sample which matches the natural tooth color is selected by doing as follows.

First, holding the handle 14 of the first triangular pillar 10 with one hand, bringing its first face 11 having weak Chroma (C1) among Chromas of 3 steps to the patient's natural tooth, and moving the triangular pillar 10 to the left and right, then selecting the color sample which matches the natural tooth color in Value from among Values of 6 steps (V0, V1, V2, V3, V4, V5) arranged in order of Value. Secondly, keeping the position of the color sample selected, in the longitudinal direction, and rotating the triangular pillar 10 to the front and back by 120 degrees, then selecting the color sample 50 which matches the natural tooth color in Chroma among Chromas of 3 steps (C1, C2, C3). At that time, 1) In the case where the value selected is V0, V1, or V5 with low occurrence rate, making the color sample having the Value and the Chroma selected and medium Hue the final selection.
2) In the case where the Value selected is V2, V3, or V4 having a high occurrence rate, taking up the triangular pillar 20 (V2), 30 (V3), or 40 (V4) each, and further
    a) In the case where the Chroma selected is weak (C1), bringing each of the color sample having medium Hue (M/C1) on the first face 21, 31, or 41 of the triangular pillar 20, 30, or 40 to the natural tooth, deciding which color sample 50 matches the natural tooth color, from among said color sample and the color samples arranged on both sides of said color sample and having yellowish Hue (Y/C1.5) or reddish Hue (R/C2.5), as the final selection.
    b) In the case where the Chroma selected is medium(C2), bringing each of the color samples having medium Hue (M/C2) on the second face 22, 32, or 42 of the triangular pillar 20, 30, or 40 to the natural tooth, deciding which color sample 50 matches the natural tooth color, from among said color sample and the color samples which are arranged on both sides of the color sample having medium Hue (M/C1 or M/C3) which appear when rotating the triangular pillar to the front and back by 120 degrees on the same position in the longitudinal direction and have yellowish Hue (Y/C1.5 or Y/C2.5) or reddish Hue (R/C1.5 or R/C2.5), in other words, deciding which color matches the natural tooth color, from among those which are on the tops of four arrows shown in Table 10, 11 and Table 12 each, as the final selection.
    c) In the case where the Chroma selected is strong (C3), bringing each of the color sample having medium Hue (M/C3) on the third face 23, 33, or 43 of the triangular pillar 20, 30, or 40 to the natural tooth, deciding which color sample 50 matches the natural tooth color, from among said color sample and the color samples arranged on both sides of said color sample and having yellowish Hue (Y/C2.5) or reddish Hue (R/C2.5), as the final selection.

In the above method, in the case where the patient's natural tooth to be compared is a mandibular anterior tooth, revising the difference of the top and the bottom between the shapes of the natural tooth and the color sample, by passing the triangular pillar from one hand to the other.

(The Effect of the Present Invention)

As described clearly above, the dental shade system in the conventional art is constituted by having many different color samples, making 20 or 3 color samples into a bundle and inserting the bundles into a single color sample rack. However, in the present invention, many different color samples are placed separately on one or plural narrow triangular pillars, each making one body.

Therefore, in the conventional art, for selecting the color sample which matches the patient's natural tooth color, it has been necessary to hold and bring the color sample rack as a whole to the patient's mouth and/or to take out and bring two or three bundles of color samples to the patient's mouth, several times. However, in the present invention, the selection of Value, Chroma, or Hue is enabled sequentially by one or two actions for each, efficiently.

In addition, in the conventional art, to distinguish which color of a pair of different color samples is closest to the natural tooth color in Value, Chroma, or Hue, it has been difficult to compare a pair of color samples with the natural tooth at equal distances and in the situation that the other color samples do not enter into the field of vision. However, in the present invention, one is enabled to compare a pair of different color samples with the natural tooth by placing them at equal distances and in the situation that the other color samples do not enter into the field of vision, simply and clearly.

Further, although the composition of the color sample arrangement of dental shade systems in the conventional art is reasonable in applying color science, the process for comparing the color samples with the natural tooth color has neither been simple nor clear. In the present invention, since the process for comparing the color samples with the natural tooth is simplified and the arrangement of the color samples is clarified, with use of the dental shade system in the present invention, the user can be enabled to perceive intuitively the three dimensional characteristic of color which man's eye senses, and it would contribute to improving the user's reproducing technique for tooth color.

TABLE 1

The basic composition of color sample arrangement of the dental shade system 111 in the conventional art

| Row No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| The 1st line | 1L/1 | 1M/1 | 1R/1 | 2L/1 | 2M/1 | 2R/1 | 3L/1 | 3M/1 | 3R/1 | 4L/1 | 4M/1 | 4R/1 | 5L/1 | 5M/1 | 5R/1 |
| The 2nd line | 1L/2 | 1M/2 | 1R/2 | 2L/2 | 2M/2 | 2R/2 | 3L/2 | 3M/2 | 3R/2 | 4L/2 | 4M/2 | 4R/2 | 5L/2 | 5M/2 | 5R/2 |
| The 3rd line | 1L/3 | 1M/3 | 1R/3 | 2L/3 | 2M/3 | 2R/3 | 3L/3 | 3M/3 | 3R/3 | 4L/3 | 4M/3 | 4R/3 | 5L/3 | 5M/3 | 5R/3 |

TABLE 2

The practical composition of color sample arrangement of the dental shade system 111 in the conventional art

| Row No. | 1 | 2 | 3 | 4 | 5 | 6 | 7 | 8 | 9 | 10 | 11 |
|---|---|---|---|---|---|---|---|---|---|---|---|
| The 1st line 115 | 1M/1 | 2L/1.5 | 2M/1 | 2R/1.5 | 3L/1.5 | 3M/1 | 3R/1.5 | 4L/1.5 | 4M/1 | 4R/1.5 | 5M/1 |

TABLE 2-continued

The practical composition of color sample arrangement of the dental shade system 111 in the conventional art

| Row No. | 1 | 2 | 3 | 4 | 5 | 6 | 7 | 8 | 9 | 10 | 11 |
|---|---|---|---|---|---|---|---|---|---|---|---|
| The 2nd line 116 | 1M/2 | X | 2M/2 | X | X | 3M/2 | X | X | 3M/2 | X | 5M/2 |
| The 3rd line 117 | X | 2L/2.5 | 2M/3 | 2R/2.5 | 3L/2.5 | 3M/3 | 3R/2.5 | 4L/2.5 | 4M/3 | 4R/2.5 | 5M/3 |

TABLE 3

The color sample arrangement on the first face 11 of the triangular pillar 10 of the dental shade system 1

| Row No. | 1 | 2 | 3 | 4 | 5 | 6 | 7 | 8 | 9 | 10 | 11 |
|---|---|---|---|---|---|---|---|---|---|---|---|
| Value | V1 | V2 | V2 | V2 | V3 | V3 | V3 | V4 | V4 | V4 | V5 |
| Chroma | C1 | C1.5 | C1 | C1.5 | C1 | C1.5 | C1 | C1.5 | C1 | C1.5 | C1.5 |
| Hue | M | Y | M | R | Y | M | R | Y | M | R | M |

TABLE 4

The color sample arrangement on the second face 12 of the triangular pillar 10 of the dental shade system 1

| Row No. | 1 | 2 | 3 | 4 | 5 | 6 | 7 | 8 | 9 | 10 | 11 |
|---|---|---|---|---|---|---|---|---|---|---|---|
| Value | V1 | X | V2 | X | X | V3 | X | X | V4 | X | V5 |
| Chroma | C2 | X | C2 | X | X | C2 | X | X | C2 | X | C2 |
| Hue | M | X | M | X | X | M | X | X | M | X | M |

TABLE 5

The color sample arrangement on the third face 13 of the triangular pillar 10 of the dental shade system 1

| Row No. | 1 | 2 | 3 | 4 | 5 | 6 | 7 | 8 | 9 | 10 | 11 |
|---|---|---|---|---|---|---|---|---|---|---|---|
| Value | X | V2 | V2 | V2 | V3 | V3 | V3 | V4 | V4 | V4 | V5 |
| Chroma | X | C2.5 | C3 | C2.5 | C2.5 | C3 | C2.5 | C2.5 | C3 | C2.5 | C3 |
| Hue | X | Y | M | R | Y | M | R | Y | M | R | M |

TABLE 6

The color sample arrangement on the first face 11 of the triangular pillar 10 of the dental shade system 1

| Row No. | 1 | 2 | ③ | 4 | ⑤ | ⑥ | 7 | ⑧ | ⑨ | 10 | ⑪ | 12 |
|---|---|---|---|---|---|---|---|---|---|---|---|---|
| Value | V0 | V1 | X | V2 | X | X | V3 | X | X | V4 | X | V5 |
| Chroma | C1 | C1 | X | C1 | X | X | C1 | X | X | C1 | X | C1 |
| Rue | M | M | X | M | X | X | M | X | X | M | X | M |

TABLE 7

The color sample arrangement on the second face 12 of the triangular pillar 10 of the dental shade system 1

| Row No. | 1 | 2 | ③ | 4 | ⑤ | ⑥ | 7 | ⑧ | ⑨ | 10 | ⑪ | 12 |
|---|---|---|---|---|---|---|---|---|---|---|---|---|
| Value | V0 | V1 | V2 | V2 | V2 | V3 | V3 | V3 | V4 | V4 | V4 | V5 |
| Chroma | C2 | C2 | C1.5 | C2 | C1.5 | C1.5 | C2 | C1.5 | C1.5 | C2 | C1.5 | C2 |
| Rue | M | M | Y | M | R | Y | M | R | Y | M | R | M |

TABLE 8

The color sample arrangement on the third face 12 of the triangular pillar 10 of the dental shade system 1

| Row No. | 1 | 2 | ③ | 4 | ⑤ | ⑥ | 7 | ⑧ | ⑨ | 10 | ⑪ | 12 |
|---|---|---|---|---|---|---|---|---|---|---|---|---|
| Value | V0 | X | V2 | V2 | V2 | V3 | V3 | V3 | V4 | V4 | V4 | V5 |
| Chroma | C3 | X | C2.5 | C3 | C2.5 | C2.5 | C3 | C2.5 | C2.5 | C3 | C2.5 | C3 |
| Rue | M | X | Y | M | R | Y | M | R | Y | M | R | M |

TABLE 9

The color sample arrangement on the first triangular pillar 10 of the dental shade system 3

| Row No. | 1 | 2 | 3 | 4 | 5 | 6 |
|---|---|---|---|---|---|---|
| Hue | M | M | M | M | M | M |
| Value | V0 | V1 | V2 | V3 | V4 | V5 |
| Chroma | | | | | | |
| Face 11 | C1 | C1 | C1 | C1 | C1 | C1 |
| Face 12 | C2 | C2 | C2 | C2 | C2 | C2 |
| Face 13 | C3 | X | C3 | C3 | C3 | C3 |

TABLE 10

The color sample arrangement on the second triangular pillar 20 of the dental shade system 3

| Row No. | 1 | 2 | 3 |
|---|---|---|---|
| Value | V2 | V2 | V2 |
| Hue/Chroma | | | |
| Face 21 | Y/C 1.5 | M/C1 | R/C1.5 |
| Face 22 | X | M/C2 | X |
| Face 23 | Y/C 2.5 | M/C3 | R/C2.5 |

TABLE 11

The color sample arrangement on the third triangular pillar 30 of the dental shade system 3

| Row No. | 1 | 2 | 3 |
|---|---|---|---|
| Value | V3 | V3 | V3 |
| Hue/Chroma | | | |
| Face 31 | Y/C 1.5 | M/C1 | R/C1.5 |
| Face 32 | X | M/C2 | X |
| Face 33 | Y/C 2.5 | M/C3 | R/C2.5 |

TABLE 12

The color sample arrangement on the fourth triangular pillar 40 of the dental shade system 3

| Row No. | 1 | 2 | 3 |
|---|---|---|---|
| Value | V4 | V4 | V4 |
| Hue/Chroma | | | |
| Face 41 | Y/C 1.5 | M/C1 | R/C1.5 |
| Face 42 | X | M/C2 | X |
| Face 43 | Y/C 2.5 | M/C3 | R/C2.5 |

What is claimed is:

1. A dental shade system, comprising:
   at least one narrow triangular pillar, upon which a plurality of different color samples are arranged with equal spacing in a field of view and in color space in terms of three dimensional coordinates of Value representing lightness level, Chroma representing color saturation, and Hue representing color,
   wherein color samples representing plural steps of Value and Hue are arranged in order in a longitudinal direction on each of three faces of said triangular pillar, and
   wherein color samples representing plural steps of Chroma are arranged radially on each of three faces of said triangular pillar, so that a user can decide the three coordinates of tooth color which match a natural tooth color.

2. The dental shade system as set forth in claim 1, wherein:
   all said color samples are arranged on one narrow triangular pillar, color samples having weak Chroma and medium Hue being arranged in order of Value on a first face of said triangular pillar leaving spaces in the longitudinal direction;
   color samples having the same Value and Chroma as each said color sample having weak Chroma and medium Hue and having more yellowish Hue and more reddish Hue than said color sample having weak Chroma and medium Hue, respectively, are arranged on either side of each said color sample having weak Chroma and medium Hue;
   color samples having the same Value and Hue as each said color sample having weak Chroma and medium Hue, are arranged on second and third faces of said triangular pillar at the same position in the longitudinal direction as each said color sample having weak Chroma and medium Hue;
   the color sample having the same Value and Hue as each said color sample having weak Chroma and medium Hue and arranged on the second face has medium Chroma; and
   the color sample having the same Value and Hue as each said color sample having weak Chroma and medium Hue and arranged on the third face has strong Chroma, respectively.

3. The dental shade system as set forth in claim 2, wherein color samples are arranged on said one triangular pillar, comprising:
   no greater than 5 steps of Value,
   no greater than 3 steps of Chroma, and
   no greater than 3 steps of Hue,
   whereby, said dental shade system comprises a maximum total of 5×3×3=45 color samples.

4. The dental shade system as set forth in claim 3, wherein:
   19 color samples having low occurrence rates are excluded;
   said maximum total of color samples is thereby reduced from 45 to 26; and
   the Chromas of a portion of said color samples are revised to amounts intermediate said steps of Chroma.

5. The dental shade system as set forth in claim 1, wherein:
   color samples having weak Chroma and medium Hue are arranged on a first face of said triangular pillar in order of Value leaving spaces in the longitudinal direction;
   color samples having the same Value and Hue as each said color sample having weak Chroma and medium Hue are arranged on second and third faces of said triangular pillar at the same position as each said color sample in the longitudinal direction;
   the color sample having the same Value and Hue as each said color sample having weak Chroma and medium Hue and arranged on the second face has medium Chroma; and
   the color sample having the same Value and Hue as each said color sample having weak Chroma and medium Hue and arranged on the third face has strong Chroma respectively;
   color samples having more yellowish Hue and more reddish Hue than each said color sample are arranged on either side of each said color sample; and a rotary mechanism is provided by which the position of each said color sample having more yellowish Hue and more reddish Hue may be rotated by hand around the axis of said triangular pillar.

6. The dental shade system as set forth in claim 5, wherein:

the number of steps of color samples arranged on said triangular pillar are set at:

no greater than 6 steps of Value (including 1 step whiter than existing tooth color);

no greater than 3 steps of Chroma; and no greater than 3 steps of Hue, wherein said dental shade system comprises a maximum total of 6×3×3=54 color samples.

7. The dental shade system as set forth in claim 6, wherein:

25 color samples with low occurrence rates are excluded;

the maximum total of color samples is thereby reduced from 54 to 29; and the Chromas of a portion of the color samples are revised to amounts intermediate said steps of Chroma.

8. The dental shade system as set forth in claim 1, wherein a plurality of different color samples are arranged separately on four said narrow triangular pillars, comprising:

a first triangular pillar, wherein color samples having weak Chroma and medium Hue are arranged in order of Value without space in the longitudinal direction on a first face of said first triangular pillar, and color samples having the same Value and Hue as each said color sample having weak Chroma and medium Hue are arranged at the same position as each said color sample having weak Chroma and medium Hue in the longitudinal direction on the second and third faces of said triangular pillar, wherein the color samples having the same Value and Hue as each said color sample having weak Chroma and medium Hue arranged on the second face have medium Chroma and the color samples having the same Value and Hue as each said color sample having weak Chroma and medium Hue arranged on the third face have strong Chroma, respectively;

a second triangular pillar, wherein, color samples the longitudinal direction on a first face of said second triangular pillar, and color samples having the same Value and Hue as each said color sample having a lightest Value among 3 steps of Value with high occurrence rates and arranged in order of yellowish Hue, medium Hue, and reddish Hue in are arranged at the same position as each said color sample having a lightest Value among 3 steps of Value with high occurrence rates and arranged in order of yellowish Hue, medium Hue, and reddish Hue in the longitudinal direction on second and third faces of said second triangular pillar, where the color samples having a lightest Value among 3 steps of Value with high occurrence rates and arranged in order of yellowish Hue, medium Hue, and reddish Hue on the second face of said second triangular pillar have medium Chroma and the color samples having a lightest Value among 3 steps of Value with high occurrence rates and arranged in order of yellowish Hue, medium Hue, and reddish Hue on the third face of said second triangular pillar have strong Chroma, respectively;

a third triangular pillar, where the color samples on said third triangular pillar are arranged replacing the first Value by the second Value from among 3 steps of Value, in the color sample arrangement of said second triangular pillar described above; and a fourth triangular pillar, where the color samples on said fourth triangular pillar are arranged replacing the first Value by the third Value from among 3 steps of Value, in the color sample arrangement of said second triangular pillar described above.

9. The dental shade system as set forth in claim 8, wherein:

the numbers of steps of color samples arranged on said four triangular pillars are set at:

no greater than 6 for Value (including 1 step whiter than existing tooth color);

no greater than 3 for Chroma; and no greater than 3 for Hue, wherein said dental shade system comprises a maximum total of 18 color samples on said first triangular pillar and 9 color samples on said second, third, and fourth triangular pillars each, totaling 18+9+9+9=45 color samples (equivalent to 36 without repetition).

10. The dental shade system as set forth in claim 9, wherein:

7 color samples having low occurrence rates are excluded;

the maximum total of color samples are thereby reduced from 45 (equivalent to 36 without repetition) to 38 (equivalent to 29 without repetition); and the Chromas of the color samples are revised in part to amounts intermediate said steps of Chroma.

11. The dental shade system as set forth in any one of claims 1–10, wherein the shape and material composition of the color samples arranged on said at least one triangular pillar resembles the natural tooth.

* * * * *